US010436706B2

United States Patent
Sasaki et al.

(10) Patent No.: US 10,436,706 B2
(45) Date of Patent: Oct. 8, 2019

(54) INFORMATION PROCESSING APPARATUS, INFORMATION PROCESSING METHOD, AND STORAGE MEDIUM

(71) Applicant: CANON KABUSHIKI KAISHA, Tokyo (JP)

(72) Inventors: Shoya Sasaki, Yokohama (JP); Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/727,904

(22) Filed: Oct. 9, 2017

(65) Prior Publication Data
US 2018/0106716 A1   Apr. 19, 2018

(30) Foreign Application Priority Data
Oct. 13, 2016   (JP) ................. 2016-202044

(51) Int. Cl.
*A61B 5/00*   (2006.01)
*G01N 21/17*   (2006.01)
(Continued)

(52) U.S. Cl.
CPC ....... *G01N 21/1702* (2013.01); *A61B 5/0095* (2013.01); *G01N 21/4795* (2013.01); *G01N 29/024* (2013.01); *G01N 29/0654* (2013.01); *G01N 29/07* (2013.01); *A61B 2562/046* (2013.01); *G01N 2021/1706* (2013.01); (Continued)

(58) Field of Classification Search
CPC ............ G01N 21/1702; G01N 21/4795; A61B 5/0033; A61B 5/0095; A61B 5/0073; A61B 5/0035; A61B 5/4312; A61B 5/708; A61B 8/4272; A61B 8/44; A61B 8/4494;
(Continued)

(56) References Cited

U.S. PATENT DOCUMENTS 6,607,489 B2 *  8/2003  Hoctor .............. A61B 8/0825
                                                        600/443
8,540,637 B2 *  9/2013  Tokita .............. A61B 5/0091
                                                        600/437
(Continued)

FOREIGN PATENT DOCUMENTS

JP        2010167258 A      8/2010

*Primary Examiner* — Hoa Q Pham
(74) *Attorney, Agent, or Firm* — Canon U.S.A., Inc. IP Division

(57) ABSTRACT

An information processing apparatus uses signals obtained by a plurality of reception units that receive an acoustic wave propagating from a point of interest to acquire object information at the point of interest. The apparatus includes a speed-of-sound acquisition unit that acquires information representing speed of sound on a propagation path of the acoustic wave, a correction unit that acquires a correction amount for the information representing speed of sound and corrects the information representing speed of sound using the correction amount, and an information acquisition unit that determines a propagation time of the acoustic wave by linearly approximating propagation paths from the point of interest to the reception units based on the corrected information and acquires the object information at the point of interest based on the signals and the propagation time.

13 Claims, 8 Drawing Sheets

(51) Int. Cl.
    *G01N 21/47*     (2006.01)
    *G01N 29/07*     (2006.01)
    *G01N 29/024*    (2006.01)
    *G01N 29/06*     (2006.01)

(52) U.S. Cl.
    CPC .............. *G01N 2021/1785* (2013.01); *G01N 2291/011* (2013.01)

(58) Field of Classification Search
    CPC ... A61B 8/0825; A61B 8/0858; A61B 8/4281; A61B 8/4483
    USPC .................................. 356/614–623, 432–440
    See application file for complete search history.

(56) References Cited

U.S. PATENT DOCUMENTS

| | | | |
|---|---|---|---|
| 9,730,589 B2* | 8/2017 | Tanaka .................. | A61B 5/0095 |
| 9,943,231 B2* | 4/2018 | Furukawa .............. | A61B 5/004 |
| 2015/0005611 A1* | 1/2015 | Mitsuhashi .......... | A61B 5/7203 |
| | | | 600/407 |
| 2016/0213257 A1* | 7/2016 | Nishihara ............. | A61B 5/0095 |
| 2017/0086680 A1* | 3/2017 | Hirata .................. | A61B 5/0095 |
| 2017/0100094 A1* | 4/2017 | Ebisawa ............... | A61B 8/0825 |
| 2017/0176399 A1* | 6/2017 | Sasaki .................... | G01N 29/30 |
| 2017/0181727 A1* | 6/2017 | Fukutani .............. | A61B 5/0095 |
| 2017/0281125 A1* | 10/2017 | Furukawa ............. | A61B 5/0095 |
| 2017/0311810 A1* | 11/2017 | Nakamura ........... | A61B 5/0095 |
| 2017/0332909 A1* | 11/2017 | Nagae .................. | A61B 8/4494 |
| 2018/0103849 A1* | 4/2018 | Iizuka .................. | A61B 5/0073 |
| 2018/0140273 A1* | 5/2018 | Terada ................. | G01S 15/894 |
| 2018/0197283 A1* | 7/2018 | Nagae .................. | A61B 5/7425 |
| 2018/0225841 A1* | 8/2018 | Sasaki .................. | A61B 5/0095 |
| 2018/0368695 A1* | 12/2018 | Nakamura ........... | A61B 5/0091 |

\* cited by examiner

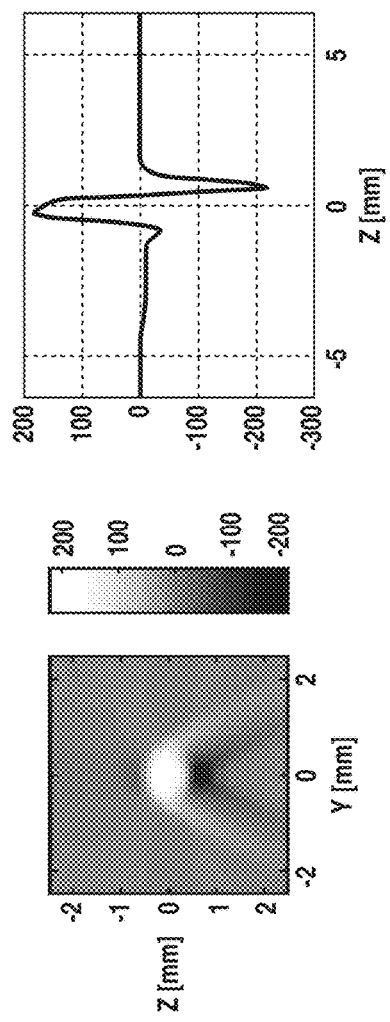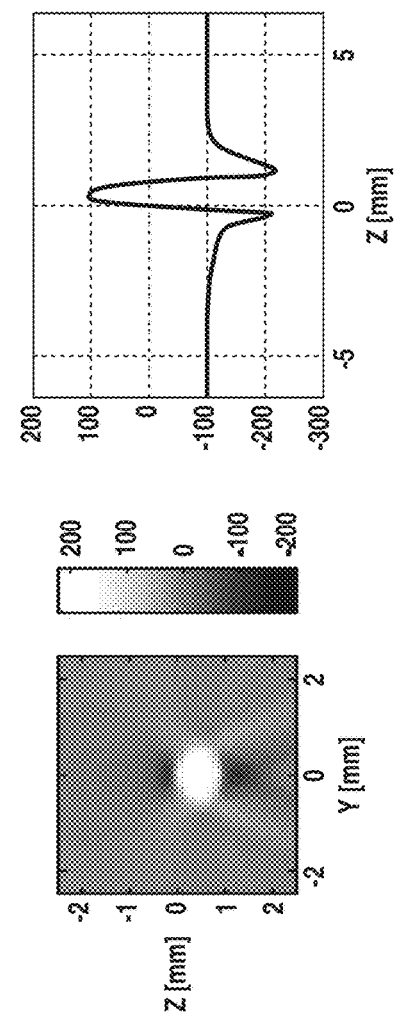
FIG. 8A
FIG. 8B

INFORMATION PROCESSING APPARATUS, INFORMATION PROCESSING METHOD, AND STORAGE MEDIUM

BACKGROUND OF THE INVENTION

Field of the Invention

The present invention relates to an information processing apparatus and an information processing method for acquiring object information based on a reception signal of an acoustic wave.

Description of the Related Art

An apparatus for performing imaging based on a reception signal of an acoustic wave propagating from an object is known. The publication of Japanese Patent Application Laid-Open No. 2010-167258 discusses a photoacoustic apparatus for acquiring information in an object, using a reception signal of an acoustic wave generated by the photoacoustic effect (also referred to as a "photoacoustic wave").

Further, it is known that an acoustic wave generated in an object is refracted when propagating through a medium having a speed-of-sound value different from that of the object. If reconstruction is performed without taking into account the influence of this refraction on the propagation time of the acoustic wave, the quality of an image to be obtained decreases.

In response, in the publication of Japanese Patent Application Laid-Open No. 2010-167258, the propagation path (also referred to as "sound ray") of a refracted acoustic wave is calculated based on Snell's law, thereby calculating the propagation time of the acoustic wave along this propagation path. Further, in the publication of Japanese Patent Application Laid-Open No. 2010-167258, reconstruction is performed based on the propagation time calculated taking the refraction into account, thereby forming an image by photoacoustic imaging.

SUMMARY OF THE INVENTION

As discussed in the publication of Japanese Patent Application Laid-Open No. 2010-167258, in a case where the propagation path of a refracted acoustic wave is calculated based on Snell's law, an enormous amount of calculation is required. Thus, it takes a lot of time to form an image.

According to an aspect of the present invention, an information processing apparatus is provided for acquiring, with a small amount of calculation, object information on which the influence of the refraction of an acoustic wave is reduced.

According to another aspect of the present invention, an information processing apparatus for, using a plurality of signals obtained by a plurality of reception units receiving an acoustic wave propagating from a point of interest in an object, acquiring object information at the point of interest includes a speed-of-sound acquisition unit configured to acquire information representing speed of sound in a medium on a propagation path of the acoustic wave, a correction unit configured to acquire a correction amount for the information representing speed of sound and correct the information representing speed of sound using the correction amount, and an information acquisition unit configured to determine a propagation time of the acoustic wave by linearly approximating propagation paths from the point of interest to the plurality of reception units based on the corrected information representing speed of sound, and acquire the object information at the point of interest based on the plurality of signals and the propagation time.

Further features of the present invention will become apparent from the following description of exemplary embodiments with reference to the attached drawings.

BRIEF DESCRIPTION OF THE DRAWINGS

FIGS. 8A and 8B are diagrams illustrating a comparative example and a simulation result according to the exemplary embodiment.

DESCRIPTION OF THE EMBODIMENTS

With reference to the drawings, exemplary embodiments of the present invention will be described below. However, the dimensions, the materials, the shapes, and the relative arrangement of the following components should be appropriately changed according to the configuration of an apparatus to which the invention is applied, or various conditions. Thus, the scope of the invention is not limited to the following description.

According to an aspect of the present invention, an acoustic wave may typically be an ultrasonic wave. Examples of the acoustic wave include waves termed a sound wave and an acoustic wave and include a photoacoustic wave, which is an acoustic wave generated by the photoacoustic effect, and an ultrasonic wave transmitted and reflected within an object. The present invention can be applied, for example, to a photoacoustic apparatus for acquiring image data based on an acoustic wave generated by the photoacoustic effect, and an ultrasonic apparatus for acquiring image data by transmitting and receiving an ultrasonic wave to and from an object.

A photoacoustic image obtained by an embodiment of the photoacoustic apparatus according to the present invention may include, for example, any image resulting from a photoacoustic wave generated by emitting light. The photoacoustic image is image data representing the spatial distribution of object information of at least one of the generation sound pressure (the initial sound pressure), the light absorption energy density, and the light absorption coefficient of the photoacoustic wave, and the concentration (the oxygen saturation) of a substance forming an object. Further, an ultrasonic image obtained by an embodiment of the ultrasonic apparatus according to the present invention may include, for example, any image resulting from an echo wave generated by transmitting an ultrasonic wave. Examples of the ultrasonic image include at least one of a B-mode image, a Doppler image, and an elastographic image. These ultrasonic images are image data representing the spatial distribution of object information based on the characteristics of an object, such as the acoustic impedance, the bloodstream, and the elasticity of the object.

The configuration of a photoacoustic apparatus and an information processing method according to a first exemplary embodiment are described below.

Figure 1:
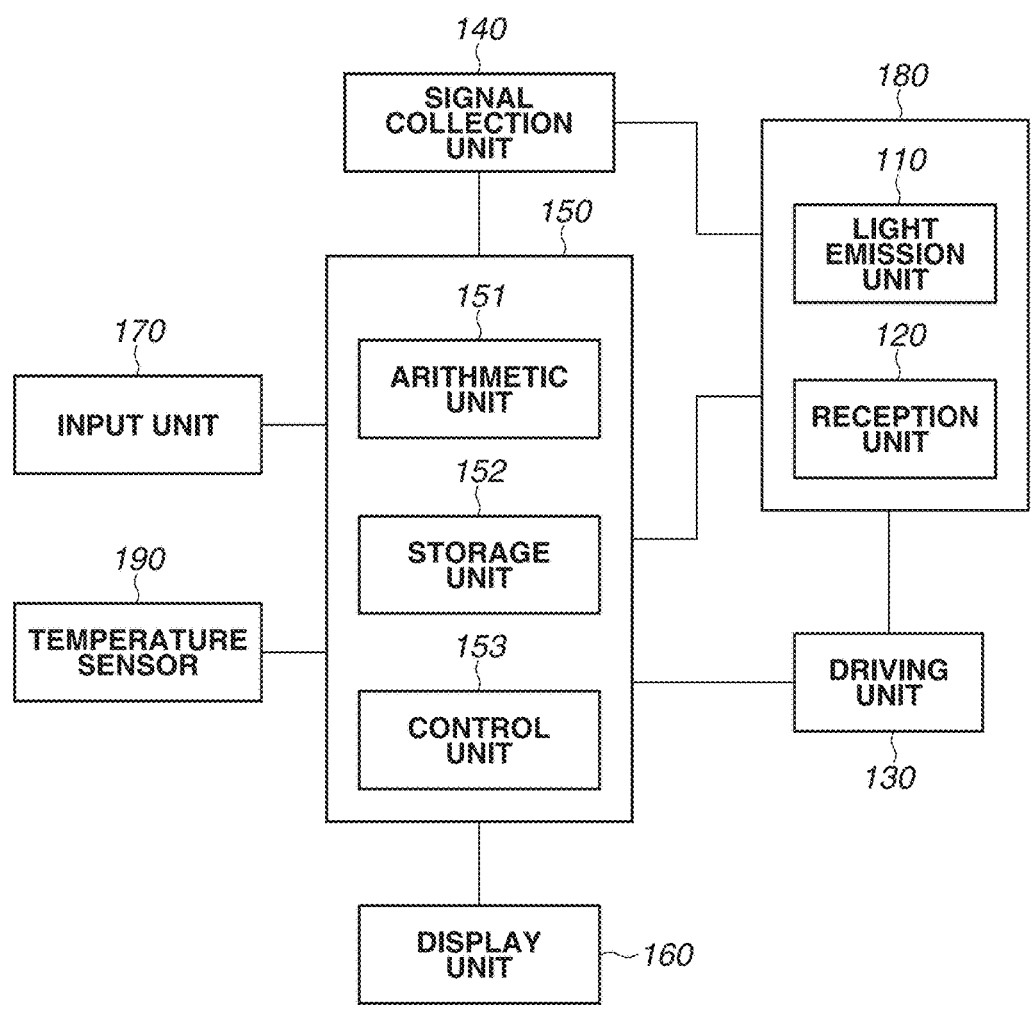
FIG. 1 is a block diagram of a photoacoustic apparatus according to an exemplary embodiment.
Figure 2A:
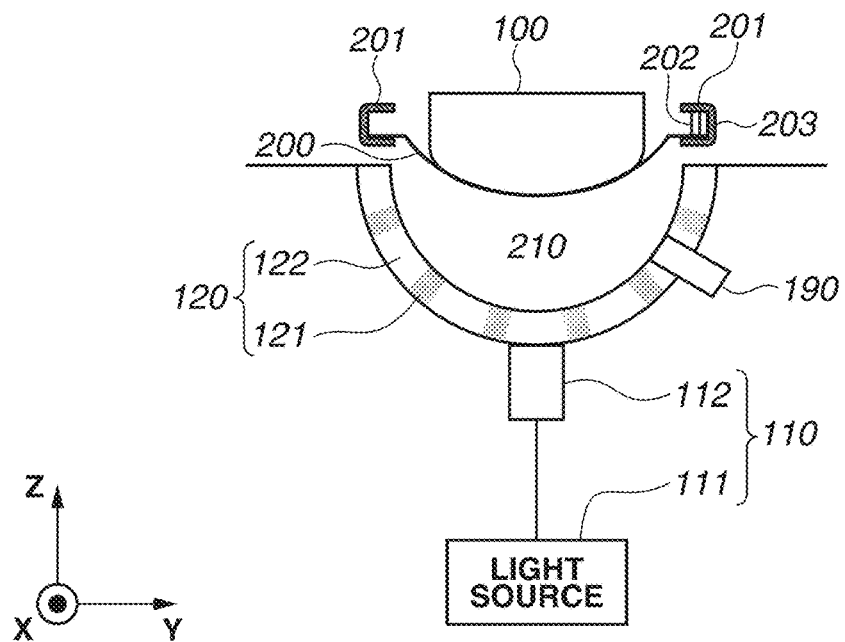
FIGS. 2A and 2B are schematic diagrams of a probe according to the exemplary embodiment.
Figure 2B:
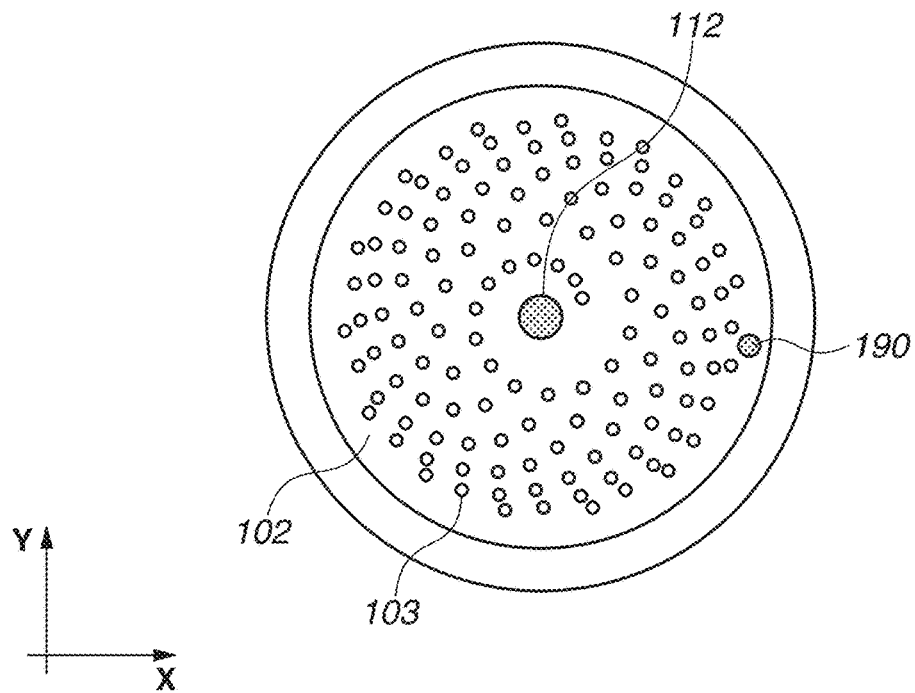

An example is described where the photoacoustic apparatus is used in the present exemplary embodiment. With reference to FIG. 1, the configuration of the photoacoustic apparatus according to the present exemplary embodiment is described. FIG. 1 is a schematic block diagram of the entirety of the photoacoustic apparatus. The photoacoustic apparatus according to the present exemplary embodiment includes a driving unit 130, a signal collection unit 140, a computer 150, a display unit 160, an input unit 170, a probe 180, and a temperature sensor 190. The probe 180 includes a light emission unit 110 and a reception unit 120. FIGS. 2A and 2B illustrate schematic diagrams of the probe 180 according to the present exemplary embodiment. A measurement target is an object 100. The driving unit 130 drives the light emission unit 110 and the reception unit 120 to perform mechanical scanning. The light emission unit 110 emits light to the object 100, and an acoustic wave is generated in the object 100. The acoustic wave generated by the photoacoustic effect due to the light is also referred to as a "photoacoustic wave". The reception unit 120 receives the photoacoustic wave, and outputs an electric signal (a photoacoustic signal) as an analog signal.

The signal collection unit 140 converts the analog signal output from the reception unit 120 into a digital signal and outputs the digital signal to the computer 150. The computer 150 stores the digital signal output from the signal collection unit 140, as signal data resulting from an ultrasonic wave or a photoacoustic wave.

The computer 150 performs signal processing on the stored digital signal, and generates image data representing a photoacoustic image. Further, the computer 150 performs image processing on the obtained image data and then outputs the image data to the display unit 160. The display unit 160 displays the photoacoustic image. A doctor or a technologist as a user can make a diagnosis by confirming the photoacoustic image displayed on the display unit 160. Based on a saving instruction from the user or the computer 150, the display image is saved in a memory in the computer 150 or a data management system connected to a modality via a network.

Further, the computer 150 also controls the driving of the components included in the photoacoustic apparatus. Further, the display unit 160 may display a graphical user interface (GUI) in addition to an image generated by the computer 150. The input unit 170 is configured to allow the user to input information. Using the input unit 170, the user can perform the operation of starting or ending a measurement, or the operation of giving an instruction to save a created image.

The information processing method according to the present exemplary embodiment corrects, based on a predetermined correction amount, information representing speed of sound acquired for use in generating image data and performs a reconstruction by linearly approximating the propagation path of the acoustic wave using the corrected information representing speed of sound. Consequently, without calculating the propagation path of an acoustic wave refracted due to the difference in speed of sound between an object as a measurement target and an acoustic matching material, it is possible, with a small amount of calculation, to reduce the influence of the refraction of the acoustic wave on image quality.

The details of the components of the photoacoustic apparatus according to the present exemplary embodiment are described below.

(Light Emission Unit 110)

The light emission unit 110 includes a light source 111, which emits light, and an optical system 112, which guides the light emitted from the light source 111 to the object 100. Examples of the light include pulse light having a square wave or a triangle wave.

The pulse width of the light emitted from the light source 111 may be a pulse width of between 1 ns and 100 ns inclusive. Further, the wavelength of the light may be a wavelength in the range of about 400 nm to 1600 nm. In a case where blood vessels are imaged at high resolution, a wavelength that is largely absorbed in the blood vessels (between 400 nm and 700 nm inclusive) may be used. In a case where a deep part of a living body is imaged, light of a wavelength that is typically less absorbed in background tissue (water or fat) of the living body (between 700 nm and 1100 nm inclusive) may be used.

As the light source 111, a laser or a light-emitting diode can be used. Further, when a measurement is made using light of a plurality of wavelengths, a light source capable of changing its wavelength may be used. In a case where a plurality of wavelengths is emitted to the object 100, it is also possible to prepare a plurality of light sources for generating light of wavelengths different from each other and alternately emit light from the light sources. Also in a case where a plurality of light sources is used, the plurality of light sources is collectively referred to as "a light source". As the laser, various lasers such as a solid-state laser, a gas laser, a pigment laser, and a semiconductor laser can be used. For example, as the light source 111, a pulse laser such as a neodymium-doped yttrium aluminum garnet (Nd:YAG) laser or an alexandrite laser may be used. Alternatively, as the light source 111, a titanium-doped sapphire (Ti:sa) laser or an optical parametric oscillator (OPO) laser, which uses Nd:YAG laser light as excitation light, may be used. Yet alternatively, as the light source 111, a flash lamp or a light-emitting diode may be used. Yet alternatively, as the light source 111, a microwave source may be used.

As the optical system 112, optical elements such as a lens, a mirror, and an optical fiber can be used. In a case where the breast is the object 100, then to emit pulse light by expanding the beam diameter of the pulse light, a light exit portion of the optical system 112 may include a diffusion plate for diffusing light. On the other hand, in a photoacoustic microscope, the light exit portion of the optical system 112 may include a lens and emit a beam by focusing the beam to increase resolution.

The light emission unit 110 may not include the optical system 112, and the light source 111 may directly emit light to the object 100.

(Reception Unit 120)

The reception unit 120 includes a transducer 121, which receives an acoustic wave and outputs an electric signal, and a supporting member 122, which supports the transducer 121. Further, the transducer 121 may be a transmission unit for transmitting an acoustic wave. A transducer as a reception unit and a transducer as a transmission unit may be a single (common) transducer, or may be separate components.

As a member forming the transducer 121, a piezoelectric ceramic material typified by lead zirconate titanate (PZT) or a piezoelectric polymer membrane material typified by polyvinylidene difluoride (PVDF) can be used. Alternatively, an element other than a piezoelectric element may be used. For example, a capacitance transducer (a capacitive micromachined ultrasonic transducer (CMUT)) or a transducer using a Fabry-Perot interferometer can be used. Any transducer may be employed so long as the transducer can receive an acoustic wave and outputs an electric signal. Further, a signal obtained by the transducer 121 is a time-resolved signal. That is, the amplitude of a signal obtained by the transducer 121 represents a value based on sound pressure (e.g., a value proportional to the sound pressure) received by the transducer 121 at each time.

Frequency components included in a photoacoustic wave are typically from 100 KHz to 100 MHz. Thus, as the transducer 121, a transducer capable of detecting these frequencies can be employed.

The supporting member 122 may be composed of a metal material having high mechanical strength. To make a large amount of emitted light incident on the object 100, a mirror surface may be provided or processing for scattering light may be performed on the surface on the object 100 side of the supporting member 122. In the present exemplary embodiment, the supporting member 122 has a hemispherical shell shape and is configured to support a plurality of transducers 121 on the hemispherical shell. In this case, the directive axes of the transducers 121 arranged in the supporting member 122 concentrate near the curvature center of the hemisphere. Then, when an image is formed using signals output from the plurality of transducers 121, the image quality near the curvature center is high. The supporting member 122 may have any configuration so long as the supporting member 122 can support the transducers 121. In the supporting member 122, the plurality of transducers 121 may be arranged on a flat surface or a curved surface termed a 1D array, a 1.5D array, a 1.75D array, or a 2D array. The plurality of transducers 121 correspond to a plurality of reception units.

Further, the supporting member 122 may function as a container for holding an acoustic matching material. That is, the supporting member 122 may be a container for placing an acoustic matching material between the transducers 121 and the object 100.

Further, the reception unit 120 may include an amplifier for amplifying a time-series analog signal output from each transducer 121. Further, the reception unit 120 may include an analog-to-digital (A/D) converter for converting the time-series analog signal output from the transducer 121 into a time-series digital signal. That is, the reception unit 120 may include the signal collection unit 140 (to be described in detail below).

Ideally, the transducers 121 may be arranged to surround the entire periphery of the object 100 so that an acoustic wave can be detected at various angles. In a case where the transducers 121 cannot be arranged to widely surround the entire periphery of the object 100, the transducers 121 may be arranged on the hemispherical supporting member 122, to provide a state close to the state where the transducers 121 surround the entire periphery of the object 100.

The placement and the number of the transducers 121 and the shape of the supporting member 122 may be optimized according to the object 100. In accordance with an aspect of the present invention, any reception unit 120 can be employed.

The space between the reception unit 120 and the object 100 is filled with a medium through which a photoacoustic wave can propagate. As this medium, a material is employed, through which an acoustic wave can propagate, of which the acoustic characteristics match at an interface with the object 100 or the transducers 121, and which has as high transmittance of a photoacoustic wave as possible. For example, as this medium, water or ultrasonic gel can be employed.

FIG. 2A illustrates a side view of the probe 180. FIG. 2B illustrates a top view of the probe 180 (as viewed from the upper direction in FIG. 2A). The probe 180 according to the present exemplary embodiment illustrated in FIG. 2A includes the reception unit 120, in which the plurality of transducers 121 are arranged three-dimensionally in the hemispherical supporting member 122, which includes an opening. Further, in the probe 180 illustrated in FIG. 2A, the light exit portion of the optical system 112 is placed in a bottom portion of the supporting member 122. Further, the probe 180 illustrated in FIG. 2A includes the temperature sensor 190, which measures the temperature of an acoustic matching material 210, which is held within the supporting member 122. FIG. 2A illustrates an example where the temperature sensor 190 is attached to the probe 180 and measures the temperature of the acoustic matching material 210 in contact with the acoustic matching material 210. Alternatively, the temperature of the acoustic matching material 210 may be measured in a non-contact manner by a temperature sensor configured separately from the probe 180. For example, as the temperature sensor 190, a contact temperature sensor such as a thermistor temperature sensor or a non-contact temperature sensor such as a radiation temperature sensor can be used.

In the present exemplary embodiment, as illustrated in FIG. 2A, the object 100 comes into contact with a retention portion 200, wherein the shape of the object 100 is retained. In the present exemplary embodiment, the following form is assumed. In a case where the object 100 is the breast, an opening into which the breast is inserted is provided in a bed for supporting a subject lying face down, and the breast hung from the opening in a vertical direction is measured.

The space between the reception unit 120 and the retention portion 200 is filled with a medium (the acoustic matching material 210) through which a photoacoustic wave can propagate. As this medium, a material is employed, through which a photoacoustic wave can propagate, of which the acoustic characteristics match at an interface with the object 100 or the transducers 121, and which has as high transmittance of a photoacoustic wave as possible. For example, as this medium, water or ultrasonic gel can be employed.

The retention portion 200 as a retention unit is used to retain the shape of the object 100 while the object 100 is measured. The retention portion 200 retains the object 100 and can restrain the movement of the object 100 and maintain the position of the object 100 within the retention portion 200. As the material of the retention portion 200, a resin material such as polycarbonate, polyethylene, or polyethylene terephthalate can be used.

It is desirable that the material of the retention portion 200 should have hardness sufficient to retain the object 100. The material of the retention portion 200 may transmit light for use in the measurement. The retention portion 200 may be composed of a material having impedance similar to that of the object 100. In a case where an object having a curved surface, such as the breast, is the object 100, the retention portion 200 may be formed into a recessed shape. In this case, the object 100 can be inserted into the recessed portion of the retention portion 200.

The retention portion 200 is attached to attachment portions 201. The attachment portions 201 may be configured so that a plurality of types of retention portions 200 can be replaced according to the size of the object 100. For example, the attachment portions 201 may be configured so that the retention portion 200 can be replaced with another retention portion 200 having a different radius of curvature or a different curvature center.

Further, in the retention portion 200, a tag 202 may be installed, in which information of the retention portion 200 is registered. For example, in the tag 202, information such as the radius of curvature, the curvature center, the speed of sound, and identification ID of the retention portion 200 can be registered. The information registered in the tag 202 is read by a reading unit 203 and transferred to the computer 150. To facilitate the reading of the tag 202 when the retention portion 200 is attached to the attachment portion 201, the reading unit 203 may be installed in the attachment portion 201. For example, the tag 202 is a barcode, and the reading unit 203 is a barcode reader.

(Driving Unit 130)

The driving unit 130 is a portion for changing the relative position between the object 100 and the reception unit 120. In the present exemplary embodiment, the driving unit 130 is a device for moving the supporting member 122 in an XY direction and is an electric XY stage in which a stepper motor is provided. The driving unit 130 includes a motor, such as a stepper motor, for generating a driving force, a driving mechanism for transmitting the driving force, and a position sensor for detecting position information of the reception unit 120. As the driving mechanism, a lead screw mechanism, a link mechanism, a gear mechanism, or a hydraulic mechanism can be used. Further, as the position sensor, a potentiometer using an encoder or a variable resistor can be used.

The driving unit 130 may change the relative position between the object 100 and the reception unit 120 not only in the XY direction (two-dimensionally), but also one-dimensionally or three-dimensionally.

The driving unit 130 may fix the reception unit 120 and move the object 100 so long as the driving unit 130 can change the relative position between the object 100 and the reception unit 120. In a case where the object 100 is moved, it is possible to employ a configuration in which the object 100 is moved by moving the retention portion 200 retaining the object 100. Alternatively, both the object 100 and the reception unit 120 may be moved.

The driving unit 130 may continuously move the relative position, or may move the relative position by a step-and-repeat process. The driving unit 130 may be an electric stage for moving the relative position on a programmed trajectory, or may be a manual stage.

Further, in the present exemplary embodiment, the driving unit 130 simultaneously drives the light emission unit 110 and the reception unit 120, and performs scanning. Alternatively, the driving unit 130 may drive only the light emission unit 110, or may drive only the reception unit 120.

(Signal Collection Unit 140)

The signal collection unit 140 includes an amplifier for amplifying an electric signal, which is an analog signal output from each transducer 121, and an A/D converter for converting the analog signal output from the amplifier into a digital signal. The signal collection unit 140 may include a field-programmable gate array (FPGA) chip. The digital signal output from the signal collection unit 140 is stored in a storage unit 152 in the computer 150. The signal collection unit 140 is also termed a data acquisition system (DAS). In the specification, an electric signal is a concept including both an analog signal and a digital signal. The signal collection unit 140 may be connected to a light detection sensor attached to a light exit portion of the light emission unit 110 and start processing in synchronization with the emission of light from the light emission unit 110 as a trigger. Further, the signal collection unit 140 may start the processing in synchronization with an instruction given using a freeze button as a trigger.

(Computer 150)

The computer 150 as an information processing apparatus includes an arithmetic unit 151, a storage unit 152, and a control unit 153. The functions of these components will be described in the description of a processing flow.

A unit having an arithmetic function as the arithmetic unit 151 can include a processor such as a central processing unit (CPU) or a graphics processing unit (GPU), or an arithmetic circuit such as an FPGA chip. This unit may include a single processor or a single arithmetic circuit, or may include a plurality of processors or a plurality of arithmetic circuits. The arithmetic unit 151 may receive various parameters such as the speed of sound in the object 100 and the configuration of the retention portion 200 from the input unit 170 and process a reception signal.

The storage unit 152 can include a non-transitory storage medium such as a read-only memory (ROM), a magnetic disk, or a flash memory. Further, the storage unit 152 may be a volatile medium such as a random-access memory (RAM). A storage medium for storing a program is a non-transitory storage medium. The storage unit 152 may include not only a single storage medium but also a plurality of storage media.

The storage unit 152 can store image data representing a photoacoustic image generated by the arithmetic unit 151 using a method described below.

The control unit 153 includes an arithmetic element such as a CPU. The control unit 153 controls the operations of the components of the photoacoustic apparatus. The control unit 153 may receive instruction signals according to various operations such as starting a measurement from the input unit 170 and control the components of the photoacoustic apparatus. Further, the control unit 153 reads a program code stored in the storage unit 152 and controls the operations of the components of the photoacoustic apparatus.

The computer 150 may be a workstation designed exclusively for the computer 150. Further, the components of the computer 150 may include different pieces of hardware. Alternatively, at least some of the components of the computer 150 may include a single piece of hardware.

Figure 3:
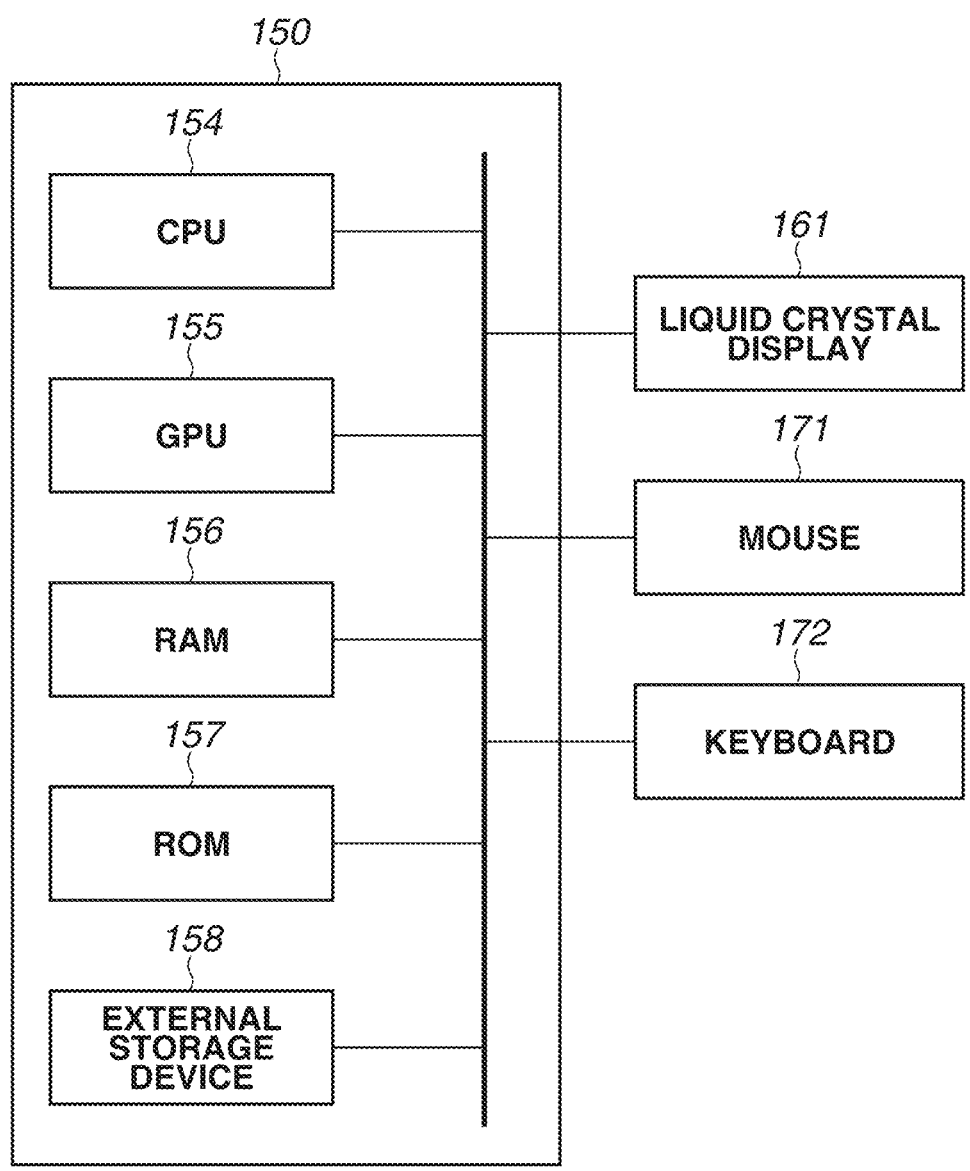
FIG. 3 is a block diagram illustrating configurations of a computer and a periphery of the computer according to the exemplary embodiment.

FIG. 3 illustrates a specific example of the configuration of the computer 150 according to the present exemplary embodiment. The computer 150 according to the present exemplary embodiment includes a CPU 154, a GPU 155, a RAM 156, a ROM 157, and an external storage device 158. Further, the computer 150 is connected to a liquid crystal display 161 as the display unit 160, and a mouse 171 and a keyboard 172 as the input unit 170.

Further, the computer 150 and the plurality of transducers 121 may be provided in a configuration in which the computer 150 and the plurality of transducers 121 are accommodated in a common housing. However, a computer accommodated in the housing may perform part of signal processing, and a computer provided outside the housing may perform the remaining signal processing. In this case, the computers provided inside and outside the housing can be collectively referred to as "a computer according to the present exemplary embodiment". That is, hardware included in the computer may not be accommodated in a single housing.

(Display Unit 160)

The display unit 160 is a display such as a liquid crystal display or an organic electroluminescent (EL) display. The display unit 160 is a device for displaying an image and a numerical value at a particular position based on object information obtained by the computer 150. The display unit 160 may display a GUI for operating an image or the apparatus. The display unit 160 may display the object information after the display unit 160 or the computer 150 has performed image processing (the adjustment of a luminance value) on the object information.

(Input Unit 170)

As the input unit 170, an operation console that can be operated by the user and includes a mouse and a keyboard can be employed. Alternatively, the display unit 160 may include a touch panel, and the display unit 160 may be used as the input unit 170.

The input unit 170 may be configured to allow the input of information used for determining a correction amount for a position or a depth to be observed, or the input of a correction amount itself. That is, the input unit 170 may be configured to allow the input of information regarding these correction amounts. As an input method, a numerical value may be input, or an input may be able to be provided by operating a slider bar. Further, a corrected image on the display unit 160 may be updated according to input information. This enables the user to set an appropriate correction amount while confirming an image corrected based on a correction amount determined by an operation of the user themselves.

The components of the photoacoustic apparatus may be configured as different devices, or may be configured as a single integrated device. Further, at least some of the components of the photoacoustic apparatus may be configured as a single integrated device.

(Object 100)

Although not included in the photoacoustic apparatus, the object 100 is described below. The photoacoustic apparatus according to the present exemplary embodiment can be used to diagnose a malignant tumor or a blood vessel disease of a person or an animal, or to perform follow-up observation of a chemical treatment. Thus, as the object 100, a diagnosis target part such as a living body, specifically the breast, each organ, a network of blood vessels, the head, the neck, the abdomen, or four limbs including fingers and toes of a human body or an animal, is assumed. For example, if a human body is a measurement target, oxyhemoglobin, deoxyhemoglobin, blood vessels including a large amount of oxyhemoglobin or deoxyhemoglobin, or new blood vessels formed near a tumor may be a target of a light absorber. Alternatively, a plaque on a carotid wall may be a target of a light absorber. Further, a pigment such as methylene blue (MB) or indocyanine green (ICG), gold microparticles, or an externally introduced substance obtained by accumulating or chemically modifying these materials may be a light absorber.

(Flow for Acquiring Object Information)

Figure 4:
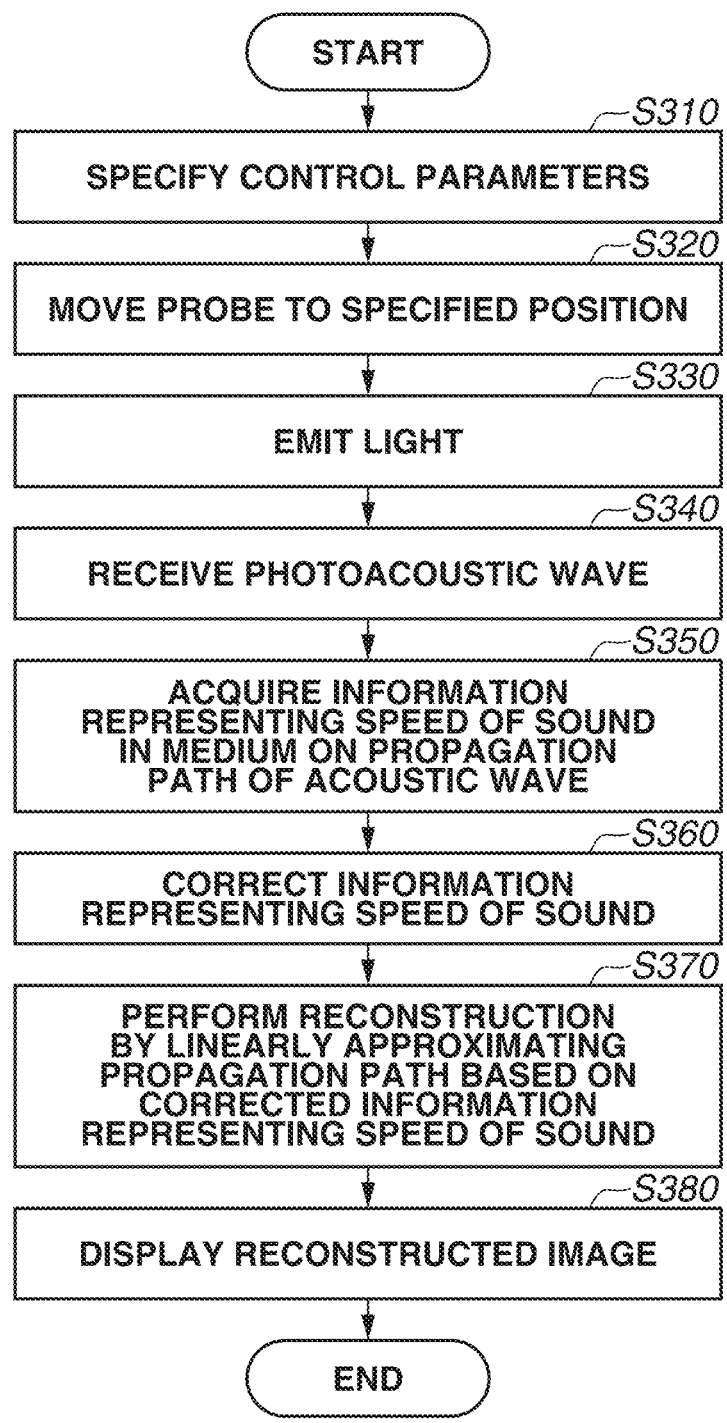
FIG. 4 is a flowchart for acquisition of object information according to the exemplary embodiment.

Next, with reference to FIG. 4, a description is given of each process of a method for acquiring object information, including the information processing according to the present exemplary embodiment. Each process is executed by the computer 150 controlling the operations of the components of the photoacoustic apparatus.

(Step S310: Process of Specifying Control Parameters)

Using the input unit 170, the user specifies control parameters, such as emission conditions (the repetition frequency and the wavelength) of the light emission unit 110 and the position of the probe 180, that are used to acquire object information.

(Step S320: Process of Moving Probe to Specified Position)

Based on the control parameters specified in step S310, the control unit 153 causes the driving unit 130 to move the probe 180 to a specified position. If the capturing of images at a plurality of positions is specified in step S310, the driving unit 130 first moves the probe 180 to a first specified position. When an instruction to start a measurement is given, the driving unit 130 may move the probe 180 to a position programmed in advance.

(Step S330: Process of Emitting Light)

Based on the control parameters specified in step S310, the light emission unit 110 emits light to the object 100.

Light generated from the light source 111 is emitted as pulse light to the object 100 through the optical system 112. Then, the pulse light is absorbed within the object 100, and a photoacoustic wave is generated by the photoacoustic effect. The light emission unit 110 transmits a synchronization signal to the signal collection unit 140 simultaneously with the transmission of the pulse light.

(Step S340: Process of Receiving Photoacoustic Wave)

If receiving the synchronization signal transmitted from the light emission unit 110, the signal collection unit 140 starts the operation of collecting a signal. That is, the signal collection unit 140 amplifies and performs AD conversion on an analog electric signal resulting from the acoustic wave and output from the reception unit 120, generating an amplified digital electric signal. Then, the signal collection unit 140 outputs the amplified digital electric signal to the computer 150. The computer 150 saves in the storage unit 152 the signal transmitted from the signal collection unit 140. If the capturing of images at a plurality of scanning positions is specified in step S310, steps S320 to S340 are repeatedly executed at the specified scanning positions, repeating the emission of pulse light and the generation of a digital signal resulting from an acoustic wave.

(Step S350: Process of Acquiring Information Representing Speed of Sound in Medium on Propagation Path of Acoustic Wave)

The computer 150 as a speed-of-sound acquisition unit acquires information representing speed of sound in a medium on the propagation path of the acoustic wave. In the present exemplary embodiment, the computer 150 acquires information representing speed of sound in the object 100 and information representing speed of sound in the acoustic matching material 210. The computer 150 acquires a speed-of-sound value $c_h$ of the object 100 and a speed-of-sound value $c_m$ of the acoustic matching material 210 as the information representing speed of sound.

Regarding the information representing speed of sound in the acoustic matching material 210, information representing speed of sound measured in advance may be stored in the storage unit 152, and in this process, the arithmetic unit 151 may read the stored information representing speed of sound from the storage unit 152, acquiring the information representing speed of sound in the acoustic matching material 210. Alternatively, a relational expression or a relationship table indicating information representing speed of sound relative to the temperature of the acoustic matching material 210 may be stored in advance in the storage unit 152. Then, in this process, the temperature sensor 190 may measure the temperature of the acoustic matching material 210, and according to the relational expression or the relationship table, the computer 150 may acquire information representing speed of sound corresponding to the measured temperature. Yet alternatively, the user may input information representing speed of sound in the acoustic matching material 210, using the input unit 170, and the computer 150 may receive the input information, acquiring the information representing speed of sound in the acoustic matching material 210.

The information representing speed of sound in the object 100 may also be acquired using a method similar to the above method for the information representing speed of sound in the acoustic matching material 210. The information representing speed of sound in the object 100, however, differs depending on each object 100. Thus, it is desirable to acquire new data for each object 100. The computer 150 may acquire the information representing speed of sound in the object 100, using a signal resulting from the acoustic wave generated from the object 100. According to this method, it is possible to acquire information representing speed of sound specific to the object 100, without making the size of the apparatus large. Further, the computer 150 may acquire the information representing speed of sound in the acoustic matching material 210, using a signal resulting from the acoustic wave generated from the object 100.

Further, if the speed-of-sound value of a medium is known from literature, the arithmetic unit 151 may read known information representing speed of sound stored in the storage unit 152, acquiring the information representing speed of sound. Further, as a method for acquiring the information representing speed of sound, the information representing speed of sound may be experimentally measured using the transmission of an ultrasonic wave, or may be measured using another modality such as ultrasonic computed tomography (CT).

In this process, any parameter may be acquired as the information representing speed of sound so long as the parameter can allow a speed-of-sound value to be obtained. For example, a speed-of-sound value can be obtained from a density p and a bulk modulus K. Thus, in this process, the density p and the bulk modulus K may be acquired as the information representing speed of sound, and a speed-of-sound value may be obtained from these parameters. Alternatively, information indicating the spatial distribution of speed-of-sound values on the propagation path of the acoustic wave propagating through the object 100 or the acoustic matching material 210 may be acquired as the information representing speed of sound.

The computer 150 may acquire the information representing speed of sound in the object 100 or the acoustic matching material 210, using another known technique.

(Step S360: Process of Correcting Information Representing Speed of Sound)

The computer 150 as a correction unit acquires a correction amount for the information representing speed of sound acquired in step S350. Then, using the acquired correction amount, the computer 150 as the correction unit corrects the information representing speed of sound acquired in step S350. In the present exemplary embodiment, the computer 150 acquires a correction amount $\Delta c_m$ for the speed-of-sound value $c_m$ of the acoustic matching material 210 and acquires a corrected speed-of-sound value $c_m + \Delta c_m$ of the acoustic matching material 210 as the corrected information representing speed of sound. That is, the computer 150 adds or subtracts the correction amount to or from the speed-of-sound value acquired in step S350, acquiring the corrected speed-of-sound value.

As a method for acquiring the correction amount, the arithmetic unit 151 may read a predetermined correction amount stored in the storage unit 152 to acquire the correction amount. Alternatively, the user may give an instruction to determine the correction amount, using the input unit 170, and based on instruction information transmitted from the input unit 170, the arithmetic unit 151 may acquire the correction amount. Yet alternatively, the arithmetic unit 151 may acquire the correction amount using a relationship table or a relational expression stored in the storage unit 152 and indicating the relationship between information for obtaining the correction amount, and the correction amount.

A description is given below of a method for determining the correction amount, the relationship table, or the relational expression to be stored in the storage unit 152, based on simulation using a calculation model illustrated in FIG. 5. First, the details of the calculation model are described. The reception unit 120 is a member in which the plurality of, namely 512, transducers 121 are arranged on an inner peripheral surface of the hemispherical supporting member 122. Each of the plurality of transducers 121 is a vibrator having a diameter of 1.5 mm. Further, as illustrated in FIG. 2B, the plurality of transducers 121 are arranged to form a three-dimensional spiral on the hemisphere. Further, the speed-of-sound value of the object 100 is set to 1600 m/s. Further, within the object 100 and at a curvature center point of the supporting member 122, a sound source having a symmetrical spherical shape with a diameter of 1 mm is installed. The space between the object 100 and the reception unit 120 is filled with water as the acoustic matching material 210. The speed-of-sound value of the acoustic matching material 210 is set to 1500 m/s. The distance from the sound source having a spherical shape with a diameter of 1 mm to the boundary between the object 100 and the acoustic matching material 210 is 15 mm.

Figure 6:
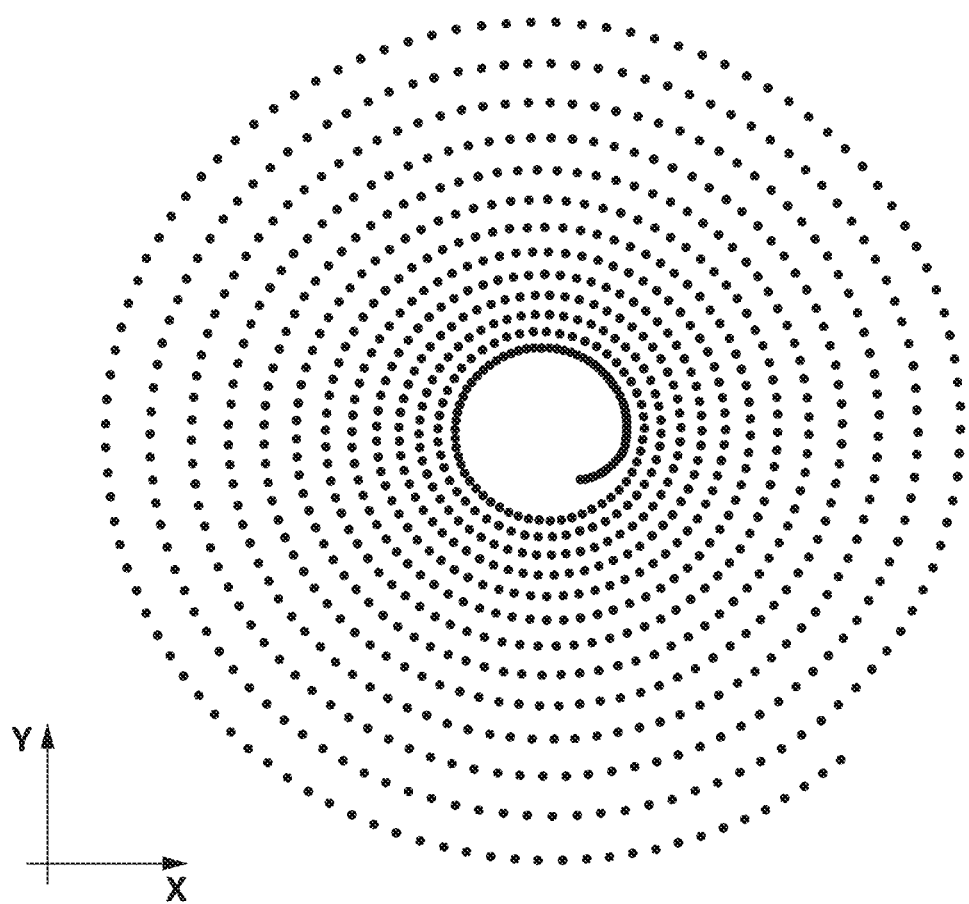
FIG. 6 is a diagram illustrating scanning positions of the probe in the simulation.

An acoustic wave generated from the sound source present at a point of interest 101 (typically, a pixel or a voxel) is received by each of the plurality of transducers 121, and a reception signal is generated by sampling the acoustic wave at a sampling frequency of 40 MHz. FIG. 6 illustrates an example where the position of the reception unit 120 (the position of the curvature center of the hemispherical supporting member 122) is plotted at the timing when light is emitted. As illustrated in FIG. 6, while moving spirally in an XY plane and changing the relative position between the reception unit 120 and the object 100, the reception unit 120 causes the plurality of transducers 121 to receive acoustic waves generated by emitting light to 1024 points.

To generate a reception signal, the arithmetic unit 151 changes a point X on the interface between the object 100 and the acoustic matching material 210 in the range of coordinates that can be taken by the point X to calculate the propagation time between the point of interest 101 and the point X, and the propagation time between the point X and each transducer 121. The arithmetic unit 151 calculates the point X at which the total of the propagation time between the point of interest 101 and the point X and the propagation time between the point X and the transducer 121 is the smallest. This point X is obtained for all transducers 121 and all points of interest 101 as calculation targets. It is assumed that the propagation path when the propagation time from the point of interest 101 to the point X to the transducer 121 is the smallest is a propagation path 103 in a case where the acoustic wave is refracted. Then, the arithmetic unit 151 generates a reception signal on the assumption that the transducer 121 receives the acoustic wave in a propagation time corresponding to the propagation path 103.

Then, using the generated reception signal, the arithmetic unit 151 generates a reconstructed image data by performing a reconstruction in accordance with a universal back-projection (UBP) method. The details of the UBP method will be described below. The number of voxels (X×Y×Z) for the reconstruction is 512×512×512, and the voxel pitch is 0.1 mm.

However, a straight line 102 (a dotted line in FIG. 5), which connects the point of interest 101 and each of the plurality of transducers 121, is different from the propagation path 103, on which the acoustic wave is actually refracted. Thus, it is understood that in a case where the reconstruction is performed by linearly approximating the propagation path of the acoustic wave (in a case where the reconstruction is performed by calculating the propagation time such that the propagation path of the acoustic wave is the straight line 102), the image quality decreases due to the refraction.

In response, the arithmetic unit 151 performs the reconstruction by changing the speed-of-sound value of the acoustic matching material 210 in a plurality of patterns and determines a speed-of-sound value for obtaining high image quality of the reconstructed image. Further, the arithmetic unit 151 determines, as a correction amount for the speed-of-sound value of the acoustic matching material 210, the difference between the speed-of-sound value for obtaining high image quality determined by thus evaluating the reconstructed image, and a setting value of the speed-of-sound value of the calculation model. The arithmetic unit 151 performs this processing on a plurality of combinations of the speed-of-sound value of the object 100, the speed-of-sound value of the acoustic matching material 210, and the position of the point of interest 101, and calculates a correction amount in each case. Then, the arithmetic unit 151 saves in the storage unit 152 a relational expression or a relationship table indicating the relationships between the combinations of the speed-of-sound value of the object 100, the speed-of-sound value of the acoustic matching material 210, and the position of the point of interest 101, and the correction amount for the acoustic matching material 210. Alternatively, the arithmetic unit 151 may save in the storage unit 152 the value of a correction amount that can be used commonly between the plurality of combinations. Then, as will be described below, the arithmetic unit 151 may read the common correction amount between the plurality of combinations from the storage unit 152 and apply the common correction amount to each combination.

In a case where the relative position between the object 100 and the reception unit 120 is moved only on the XY plane by the driving unit 130, a correction amount tends to have higher sensitivity in the Z-direction (the depth direction) than in the XY direction. Thus, a common correction amount may be applied to a plane at a depth including the point of interest 101. Further, a common correction amount may also be applied to a depth near a depth including the point of interest 101. That is, a common correction amount may be applied to a particular depth, or to a plurality of points of interest present at a particular depth and a depth near the particular depth. It is possible to reduce data capacity for the correction amount, the relationship table, or the relational expression to be stored in the storage unit 152.

As a method for evaluating the image quality of the reconstructed image, the user may confirm information regarding a reconstructed image (an image itself or a line profile of the image intensity) and specify a reconstructed image having high image quality as reference for a correction amount, using the input unit 170. Alternatively, the arithmetic unit 151 may evaluate image quality based on the reconstructed image. For example, the arithmetic unit 151 may generate a line profile of the image intensity of the reconstructed image, evaluate the difference in image intensity between extrema at two low points on the line profile that appear at both ends of a peak of the image intensity, and evaluate that the smaller the difference in image intensity, the higher the image quality. In this technique, the symmetry of the line profile is evaluated using a unique image feature occurring by reconstruction in accordance with the UBP method, and the image quality is evaluated. In addition to this, any method can be employed so long as the method can evaluate the image quality of the reconstructed image.

As described above, the user may give an instruction to determine the correction amount using the input unit 170, and based on instruction information transmitted from the input unit 170, the arithmetic unit 151 may acquire the correction amount. Using the input unit 170, the user can indicate the value of the correction amount, or indicate information used to determine the correction amount. Examples of the information that can be used to determine the correction amount include the information representing speed of sound in the medium on the propagation path of the acoustic wave (e.g., the information representing speed of sound in the object 100 or the acoustic matching material 210), and a point of interest to be corrected. The arithmetic unit 151 can determine the correction amount based on these pieces of instruction information, and a relationship table or a relational expression stored in the storage unit 152 and indicating the relationships between these pieces of information and the correction amount. With reference to FIGS. 7A to 7D, a description is given below of an example of a GUI displayed on the display unit 160 in a case where the user gives an instruction to determine the correction amount, using the input unit 170.

Figure 7A:
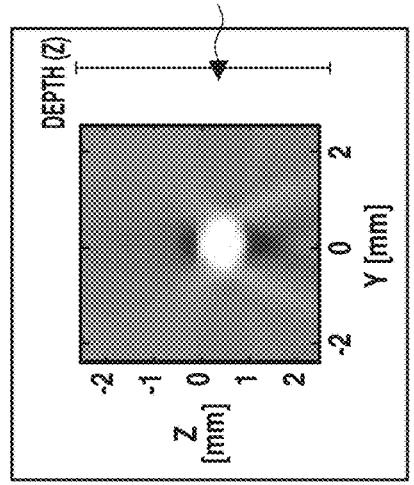
FIGS. 7A, 7B, 7C, and 7D are diagrams illustrating a graphical user interface (GUI) according to the exemplary embodiment.
Figure 7B:
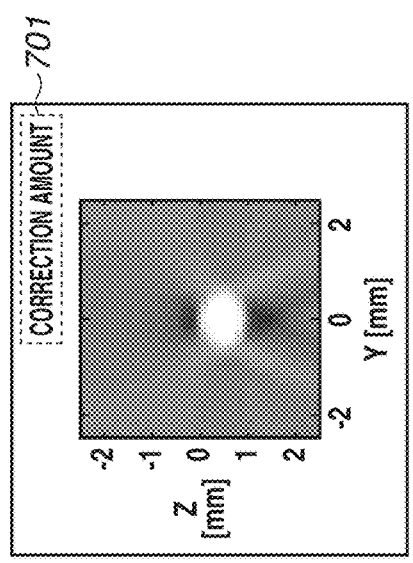
Figure 7C:
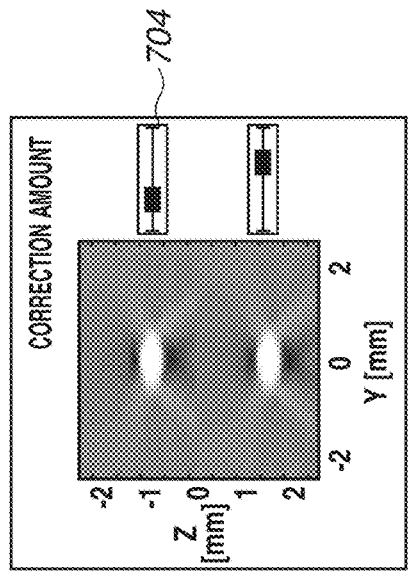
Figure 7D:
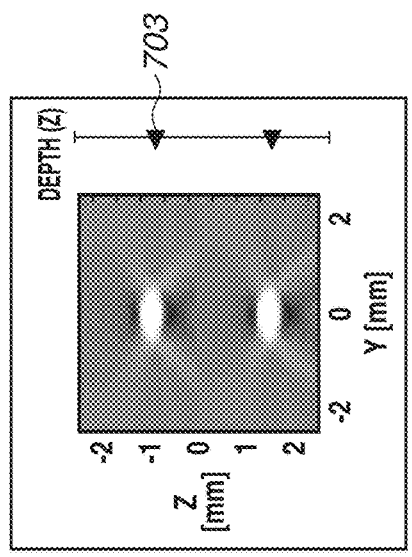

For example, as illustrated in FIG. 7A, the user may input the value of the correction amount to a text box 701 on the GUI, using the input unit 170. As illustrated in FIG. 7B, the user may operate a slide bar 702, which enables the user to specify a depth (a position in the Z-direction) in an image, indicating a depth including a point of interest to be corrected. Further, as illustrated in FIG. 7C, the user may operate a slide bar 703, obtaining a plurality of depths including points of interest to be corrected. Further, as illustrated in FIG. 7D, the user may be able to operate slide bars 704 to indicate correction amounts for the depths specified in FIG. 7B or FIG. 7C.

The "depth direction" refers to the directive direction of the reception unit 120 relative to the acoustic wave. In the present exemplary embodiment, the "depth direction" refers to an out-of-plane direction (an up-down direction in FIG. 2A) of the opening of the hemispherical supporting member 122. Further, in a case where the plurality of transducers 121 are arranged two-dimensionally, the depth direction is an out-of-plane direction of the surface on which the transducers 121 are arranged.

The correction amount may be a correction amount for any medium on the propagation path of the acoustic wave. The correction amount may be acquired for a single medium, or the correction amount may be acquired for a plurality of media. It is desirable to acquire the correction amount for a medium having a long propagation distance, which has great influence on a propagation time due to refraction. In the case of the present exemplary embodiment, typically, the distance at which the photoacoustic wave propagates through the acoustic matching material 210 is longer than the distance at which the photoacoustic wave propagates through the object 100. Thus, a correction amount for correcting only the information representing speed of sound in the acoustic matching material 210 may be acquired. Further, in a case where the relationship between the temperature and the speed-of-sound value of a material forming the acoustic matching material 210 is known, a speed-of-sound value determined based on temperature information of the acoustic matching material 210 may be corrected based on the correction amount in this process. On the other hand, a substance forming the object 100 has an individual difference. Thus, the information representing speed of sound in the object 100 may be acquired by a method different from the method using temperature information, and may not be corrected.

(Step S370: Process of Performing Reconstruction by Linearly Approximating Propagation Path Based on Corrected Information Representing Speed of Sound)

Based on the reception signal acquired in step S340 and the information representing speed of sound corrected in step S360, the computer 150 as an information acquisition unit performs the reconstruction by linearly approximating the propagation path of the acoustic wave, acquiring object information at the point of interest 101. The computer 150 acquires object information at a plurality of points of interest and can acquire the spatial distribution (image data) of the object information.

For example, as a reconstruction technique for acquiring the generation sound pressure (the initial sound pressure) of the acoustic wave as the object information, the arithmetic unit 151 may employ the UBP method represented by expression (1).

$$p_0(r_0) = \frac{\sum_i^N b\left(r_i, t = \frac{|r_i - r_0|}{c}\right) \cdot \Delta\Omega_i}{\sum_i^N \Delta\Omega_i} \quad (1)$$

$$b(r, t) = 2p(r, t) - 2t\frac{\partial p(r, t)}{\partial t}$$

In this expression, $r_0$ represents a position vector indicating the position where the reconstruction is performed (also referred to as a "reconstruction position" or a "point of interest"), $p_0(r_0,t)$ represents the initial sound pressure at the position where the reconstruction is performed, and c represents the speed of sound on the propagation path. Further, $\Delta\Omega_i$ represents a solid angle for estimating an i-th transducer 121 from the position where the reconstruction is performed, and N represents the number of transducers 121 for use in the reconstruction. Expression (1) indicates that processing such as differentiation is performed on a reception signal $p(r_i,t)$, and the processing result is multiplied by the weight of the solid angle in performing phased addition (back projection). In expression (1), t represents a time (a propagation time) in which the photoacoustic wave propagates on a sound ray connecting the point of interest 101 and each transducer 121. When $b(r_i,t)$ is calculated, another type of arithmetic processing may be performed. For example, frequency filtering (low-pass, high-pass, or band-pass filtering), deconvolution, envelope detection, or wavelet filtering may be performed. Further, in accordance with an aspect of the present invention, any reconstruction algorithm may be used so long as the method enables the reconstruction to be performed by obtaining the propagation time on the sound ray connecting each transducer 121 and the point of interest 101. For example, as a back projection method in a time domain, filtered back projection (FBP) or phased addition (delay-and-sum) may be employed.

Figure 5:
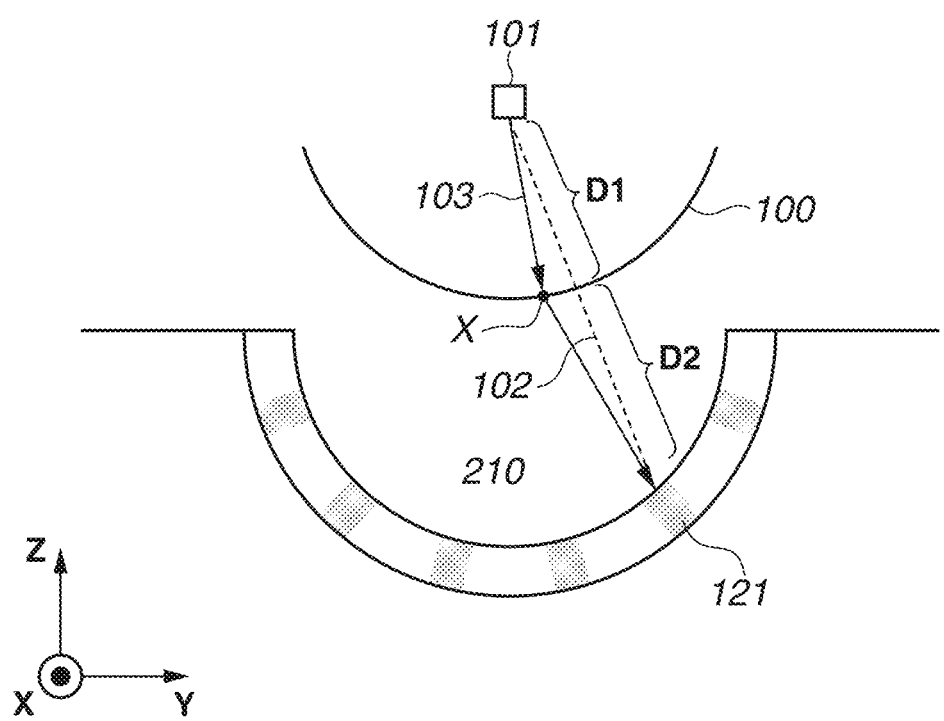
FIG. 5 is a diagram illustrating a calculation model for simulation.

FIG. 5 illustrates a sound ray (propagation path) 102, which is obtained by linearly approximating the propagation path of the acoustic wave from the point of interest 101 to each transducer 121. When the propagation path is linearly approximated, the propagation distance in the object 100 is D1, and the propagation distance in the acoustic matching material 210 is D2. In this case, the propagation time t in expression (1) can be represented by expression (2).

$$t = \frac{D1}{c_h} + \frac{D2}{c_m + \Delta c_m} \quad (2)$$

In this expression, D1 represents the propagation distance in the object 100 when the propagation path is linearly approximated. D2 represents the propagation distance in the acoustic matching material 210 when the propagation path is linearly approximated. D1 and D2 are determined based on position information of the transducer 121 when receiving the acoustic wave. The position information of the transducer 121 may be acquired based on position information of the reception unit 120 output from the driving unit 130 when a synchronization signal is received from the light emission unit 110. Further, the position information of the transducer 121 may be acquired based on an output from a position acquisition unit such as a magnetic sensor included in the reception unit 120.

Further, $c_h$ represents the speed-of-sound value of the object 100, and the value acquired in step S350 is used in the present exemplary embodiment. $c_m$ represents the speed-of-sound value of the acoustic matching material 210. $\Delta c_m$ represents a correction amount for the speed-of-sound value of the acoustic matching material 210. Further, $c_m + \Delta c_m$ represents the corrected speed-of-sound value of the acoustic matching material 210, and the value acquired in step S360 is used in the present exemplary embodiment.

In the present exemplary embodiment, as illustrated in expressions (1) and (2), using corrected information representing speed of sound in a medium on the propagation path of an acoustic wave, the arithmetic unit 151 performs the reconstruct by linearly approximating the propagation path of the acoustic wave to acquire object information at the point of interest 101. According to this method, it is possible to omit calculation used to calculate the propagation path of a refracted acoustic wave. Further, information representing speed of sound is corrected, and the reconstruction is performed by linearly approximating the propagation path based on the corrected information representing speed of sound, and it is possible to suppress a decrease in the acquisition accuracy of object information due to the linear approximation.

(Step S380: Process of Displaying Reconstructed Image)

The computer 150 as a display control unit transmits the image data acquired in step S370 to the display unit 160 and causes the display unit 160 to display the image data as the reconstructed image. In addition to displaying the image data of the object information as an image, the computer 150 may display a numerical value of the object information at a particular position of the image data. Further, the computer 150 may display in parallel a reconstructed image obtained based on information representing speed of sound before being corrected and a reconstructed image obtained based on information representing speed of sound after being corrected, or display these reconstructed images by in a switching manner.

A description is given of the calculation result of the simulation performed to describe the effects of the information processing method according to the present exemplary embodiment. In this simulation, the calculation model illustrated in FIG. 5 was used.

First, as a comparative example, FIG. 8A illustrates a reconstructed image obtained in a case where the reconstruction is performed by linearly approximating the propagation path using setting values in the simulation such that the speed-of-sound value of the object 100 is 1600 m/s, and the speed-of-sound value of the acoustic matching material 210 is 1500 m/s. Further, FIG. 8A also illustrates a line profile of the image intensity in the Z-direction in a case where Y=0. In view of the line profile illustrated in FIG. 8A, the symmetrical sound source is asymmetrically imaged, and an artifact occurs in the positive Z-direction. Thus, it is understood that the image quality decreases due to the influence of refraction.

Next, FIG. 8B illustrates a reconstructed image obtained by the technique according to the present exemplary embodiment. In this method, a correction amount of +4.5 m/s for the speed-of-sound value of the acoustic matching material 210 is used, which corresponds to the combination of a speed-of-sound value of 1600 m/s of the object 100, a speed-of-sound value of 1500 m/s of the acoustic matching material 210, and a depth of 15 mm, which corresponds to the point of interest 101. Using this correction amount, the reconstruction was performed by linearly approximating the propagation path of the acoustic wave such that the speed-of-sound value of the object 100 was 1600 m/s, and the corrected speed-of-sound value of the acoustic matching material 210 was 1504.5 m/s. As a result, the reconstructed image illustrated in FIG. 8B was obtained. In the reconstructed image illustrated in FIG. 8B, a line profile of the image intensity in the Z-direction in a case where Y=0 is symmetrical, and an artifact in the positive Z-direction decreases, as compared with FIG. 8A. That is, in the technique according to the present exemplary embodiment, it is understood that a decrease in the image quality of the reconstructed image due to refraction is suppressed.

In this simulation, the number of the plurality of transducers 121 is 512, the number of scanning positions of the reception unit 120 is 1024, and the number of voxels in a reconstruction region is 512×512×512. Thus, to calculate the propagation path of an acoustic wave due to refraction based on Snell's law with respect to each point of interest, it is necessary to make 512×1024×512×512 calculations. Thus, this method requires an enormous amount of calculation, which leads to the lengthening of the reconstruction time.

On the other hand, in the case of the technique according to the present exemplary embodiment, the reconstruction is performed by linearly approximating the propagation path based on corrected information representing speed of sound. Thus, without calculating the propagation path of a refracted acoustic wave, which would require an enormous amount of calculation, it is possible to suppress a decrease in the image quality due to the refraction.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-202044, filed Oct. 13, 2016, which is hereby incorporated by reference herein in its entirety.

What is claimed is:

1. An information processing apparatus for, using a plurality of signals obtained by a plurality of reception units receiving an acoustic wave propagating from a point of interest in an object, acquiring object information at the point of interest, the information processing apparatus comprising:
    a speed-of-sound acquisition unit configured to acquire information representing speed of sound in a medium on a propagation path of the acoustic wave;
    a correction unit configured to acquire a correction amount for the information representing speed of sound and correct the information representing speed of sound based on the correction amount; and
    an information acquisition unit configured to determine a propagation time of the acoustic wave by linearly approximating propagation paths from the point of interest to the plurality of reception units based on the corrected information representing speed of sound, and to acquire the object information at the point of interest based on the plurality of signals and the propagation time.

2. The information processing apparatus according to claim 1, further comprising a storage unit in which the correction amount is stored,
    wherein the correction unit is configured to acquire the correction amount by reading the correction amount from the storage unit.

3. The information processing apparatus according to claim 1, further comprising a storage unit in which a relationship table or a relational expression indicating relationships between the information representing speed of sound, position information of the plurality of reception units, position information of the point of interest, and the correction amount is stored,
  wherein the correction unit is configured to acquire the position information of the plurality of reception units and the position information of the point of interest, read the relationship table or the relational expression from the storage unit, and acquire the correction amount based on the information representing speed of sound, the position information of the plurality of reception units, the position information of the point of interest, and the relationship table or the relational expression.

4. The information processing apparatus according to claim 3, wherein the correction unit is configured to acquire the position information of the point of interest determined based on an instruction from a user.

5. The information processing apparatus according to claim 1, wherein the correction unit is configured to acquire the correction amount based on an instruction from a user.

6. The information processing apparatus according to claim 1,
  wherein the speed-of-sound acquisition unit is configured to acquire the information representing speed of sound based on temperature information of the medium measured by a temperature sensor, and
  wherein the correction unit is configured to correct the information representing speed of sound acquired based on the temperature information.

7. The information processing apparatus according to claim 6,
  wherein the medium includes the object and an acoustic matching material placed between the object and the plurality of reception units,
  wherein the speed-of-sound acquisition unit is configured to acquire information representing speed of sound in the acoustic matching material based on temperature information of the acoustic matching material measured by the temperature sensor,
  wherein the correction unit is configured to correct the information representing speed of sound in the acoustic matching material acquired based on the temperature information, and
  wherein the information acquisition unit is configured to determine the propagation time of the acoustic wave by linearly approximating the propagation paths from the point of interest to the plurality of reception units based on the corrected information representing speed of sound in the acoustic matching material and information representing speed of sound in the object acquired by the speed-of-sound acquisition unit.

8. The information processing apparatus according to claim 1,
  wherein based on the correction amount, the correction unit is configured to correct the information representing speed of sound with respect to a plurality of the points of interest present at a particular depth,
  wherein the information acquisition unit is configured to determine the propagation time corresponding to the plurality of the points of interest by linearly approximating propagation paths from the plurality of the points of interest to the plurality of reception units based on the corrected information representing speed of sound corresponding to the plurality of the points of interest, and
  wherein the information acquisition unit is configured to acquire the object information at the plurality of the points of interest based on the plurality of signals and the propagation time corresponding to the plurality of the points of interest.

9. The information processing apparatus according to claim 1,
  wherein based on the correction amount, the correction unit is configured to correct the information representing speed of sound with respect to a plurality of the points of interest present at a particular depth or a depth near the particular depth,
  wherein the information acquisition unit is configured to determine the propagation time corresponding to the plurality of the points of interest by linearly approximating propagation paths from the plurality of the points of interest to the plurality of reception units based on the corrected information representing speed of sound corresponding to the plurality of the points of interest, and
  wherein the information acquisition unit is configured to acquire the object information at the plurality of the points of interest based on the plurality of signals and the propagation time corresponding to the plurality of the points of interest.

10. The information processing apparatus according to claim 1, further comprising a light emission unit configured to emit light to the object,
  wherein the plurality of reception units is configured to receive an acoustic wave generated by the emission of the light, and to output the plurality of signals.

11. The information processing apparatus according to claim 1, further comprising a transmission unit configured to transmit an ultrasonic wave to the object,
  wherein the plurality of reception units is configured to receive an acoustic wave generated by the ultrasonic wave being reflected within the object, and to output the plurality of signals.

12. An information processing method for, using a plurality of signals obtained by a plurality of reception units receiving an acoustic wave propagating from a point of interest in an object, acquiring object information at the point of interest, the information processing method comprising:
  acquiring information representing speed of sound in a medium on a propagation path of the acoustic wave;
  acquiring a correction amount for the information representing speed of sound;
  correcting the information representing speed of sound using the correction amount;
  determining a propagation time of the acoustic wave by linearly approximating propagation paths from the point of interest to the plurality of reception units based on the corrected information representing speed of sound; and
  acquiring the object information at the point of interest based on the plurality of signals and the propagation time.

13. A storage medium for storing a program for causing a computer to execute the information processing method according to claim 12.

* * * * *